Figure 1:
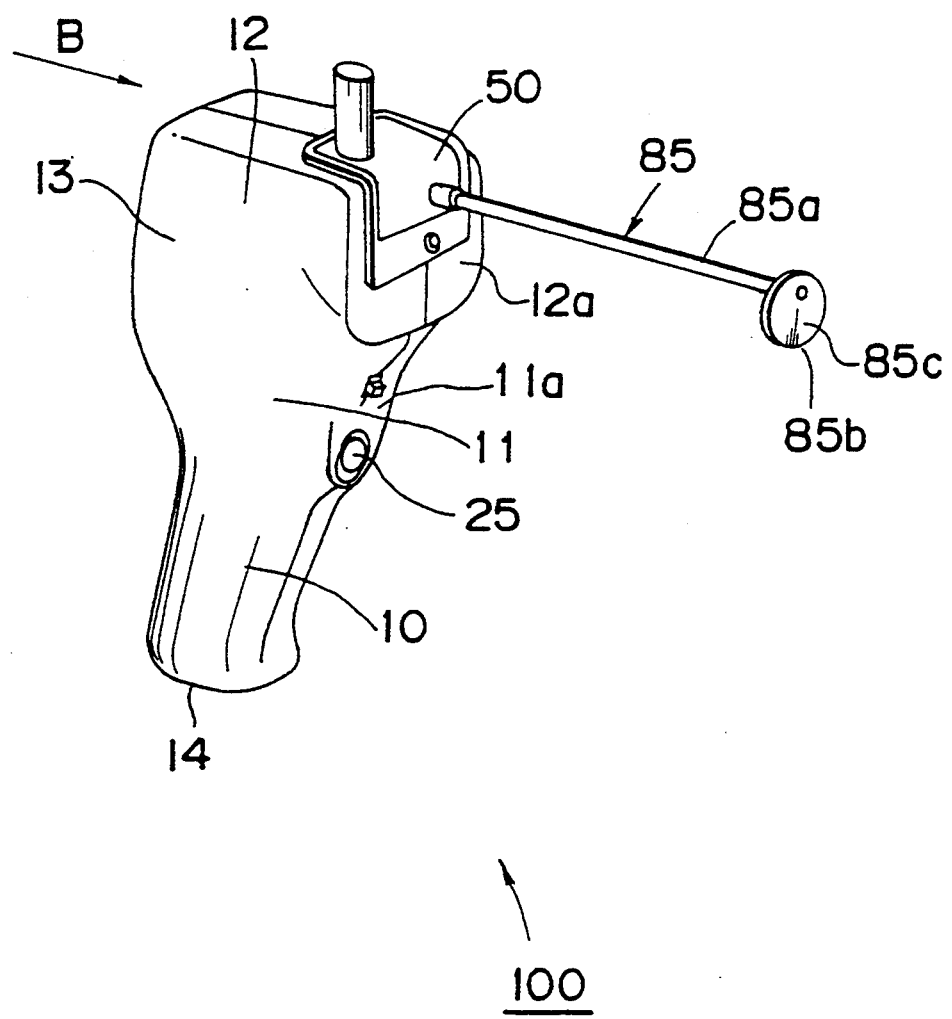
Figure 2:
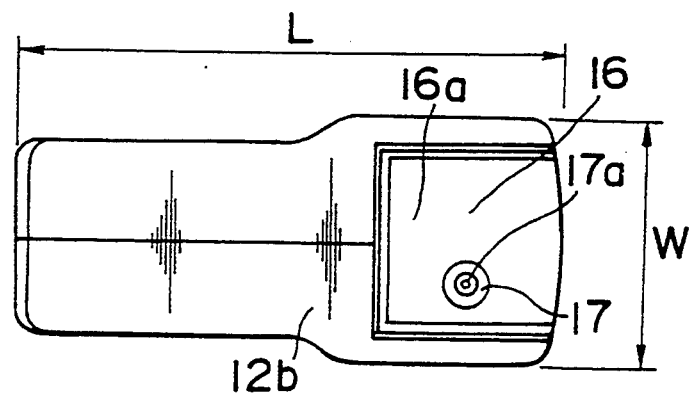
Figure 3:
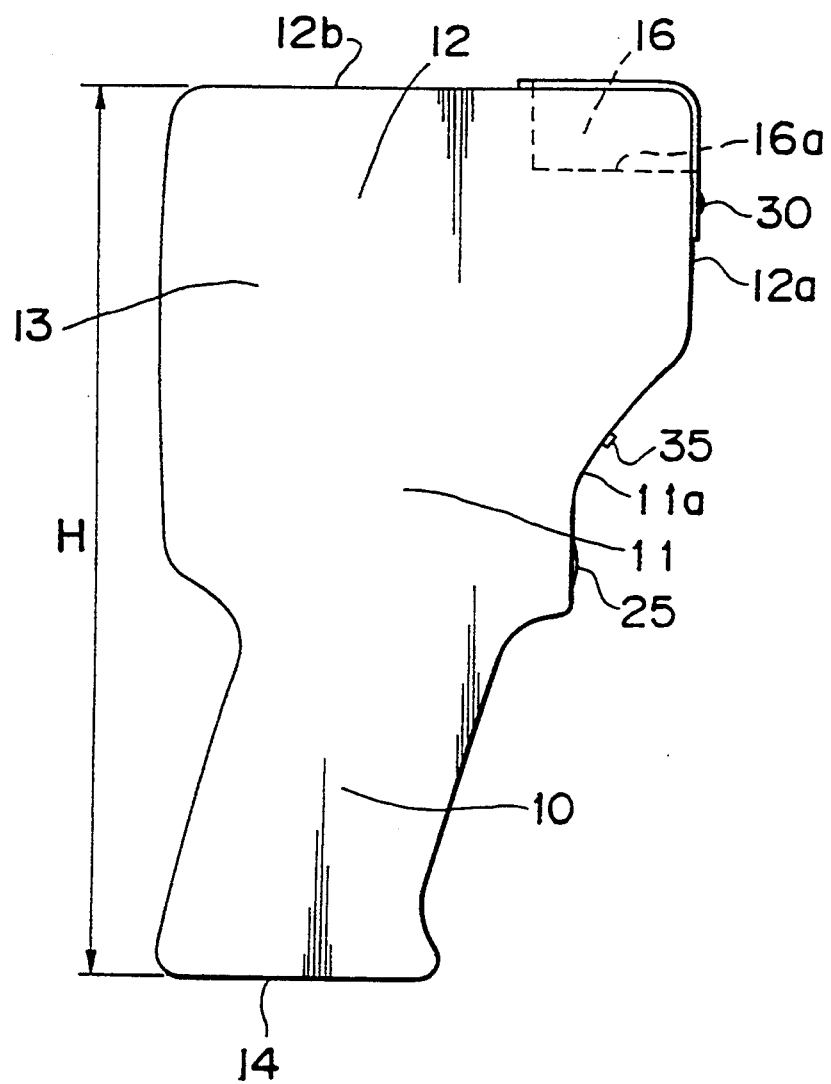
Figure 4:
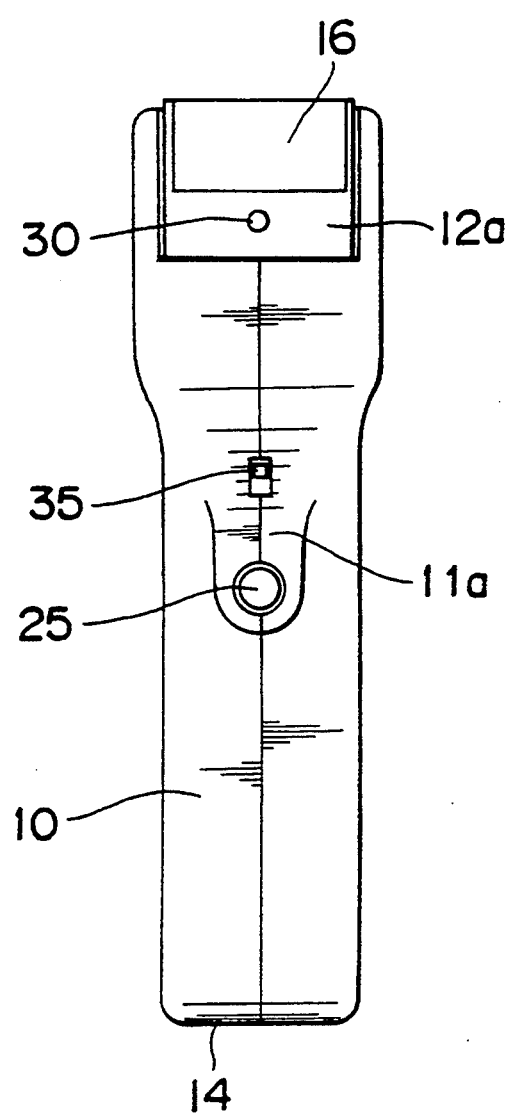

United States Patent [19]
Terakura et al.

[11] Patent Number: 5,445,612
[45] Date of Patent: Aug. 29, 1995

[54] POWDERED MEDICAMENT-MIXED GAS INJECTING APPARATUS AND POWDERED MEDICAMENT-MIXED GAS INJECTING NOZZLE TO BE CONNECTED TO THE SAME

[75] Inventors: Seiji Terakura, Ikoma; Toyoyuki Maeda, Kawachinagano, both of Japan

[73] Assignee: Kaigen Co., Ltd., Osaka, Japan

[21] Appl. No.: 313,589

[22] Filed: Sep. 29, 1994

[30] Foreign Application Priority Data

Oct. 4, 1993 [JP] Japan ................................. 5-247826

[51] Int. Cl.$^6$ ............................................. A61M 13/00
[52] U.S. Cl. ....................................... 604/58; 604/24
[58] Field of Search ................ 604/58, 57, 207, 208, 604/187, 215, 216, 23, 24, 239

[56] References Cited

U.S. PATENT DOCUMENTS

| | | | |
|---|---|---|---|
| 4,184,258 | 1/1980 | Barrington et al. | 604/58 X |
| 4,534,345 | 8/1985 | Wetterlin | 604/58 X |
| 5,273,531 | 12/1993 | Knoepfler | 604/58 |
| 5,312,333 | 5/1994 | Churinetz et al. | 604/58 X |

FOREIGN PATENT DOCUMENTS

| | | |
|---|---|---|
| 3108918 | 9/1982 | Germany . |
| 4-22109 | 4/1992 | Japan . |
| 257250 | 9/1948 | Switzerland . |
| WO85/02346 | 6/1985 | WIPO . |

OTHER PUBLICATIONS

Digestive Endoscopy, Dig. Endosc. 1993; 5:218–223, Teruo Hoshino et al.
Alto Shooter, Catalogue issued on Jun., 1994.

*Primary Examiner*—John F. Yasko

[57] ABSTRACT

A powdered medicament-mixed gas injecting apparatus includes a first passage having a gas supply opening at one end thereof for supplying gas. A second passage includes a container-fitting end portion at one end thereof for fitting thereto a container opening of a powdered medicament container in which powdered medicament is accommodated. One end is closed and the other end is provided with the container opening. The other end of the second passage is coupled with the other end of the first passage. The second passage serves for introducing supply gas fed from the gas supply opening of the first passage to the powdered medicament container, and for introducing powdered medicament-mixed gas which has been formed by mixing the supply gas with the powdered medicament in a direction opposite to a direction in which the supply gas is fed. The second passage allows gas to pass bidirectionally therethrough. A third passage includes one end thereof coupled with a coupling portion at which the respective other ends of the first and second passages are coupled with each other. The third passage is branched from the coupling portion. The third passage includes at the other end thereof a third passage opening for jetting out the powered medicament-mixed gas to introduce the powdered medicament-mixed gas.

19 Claims, 9 Drawing Sheets

FROM AIR PUMP

POWDERED MEDICAMENT-MIXED GAS INJECTING APPARATUS AND POWDERED MEDICAMENT-MIXED GAS INJECTING NOZZLE TO BE CONNECTED TO THE SAME

BACKGROUND OF THE INVENTION

1. Field of the Invention

The present invention relates to a powdered medicament-mixed gas injecting apparatus and a powdered medicament-mixed gas injecting nozzle for injecting powdered, for example, hemostatic powdered medicament to an affected part, for example, in the body.

2. Conventional Art

When tissue of a specified portion in the body in picked up, for example, for tissue examination, there may occur bleeding at the pick-up portion. In such a case, it has been conventional practice to leave the bleeding as it is, without stopping blood, so that the bleeding will be naturally cured. There have been reported examples in which hemostatic powdered medicament are injected to the affected part by using a powder-feeding apparatus which is described below.

Figure 13:
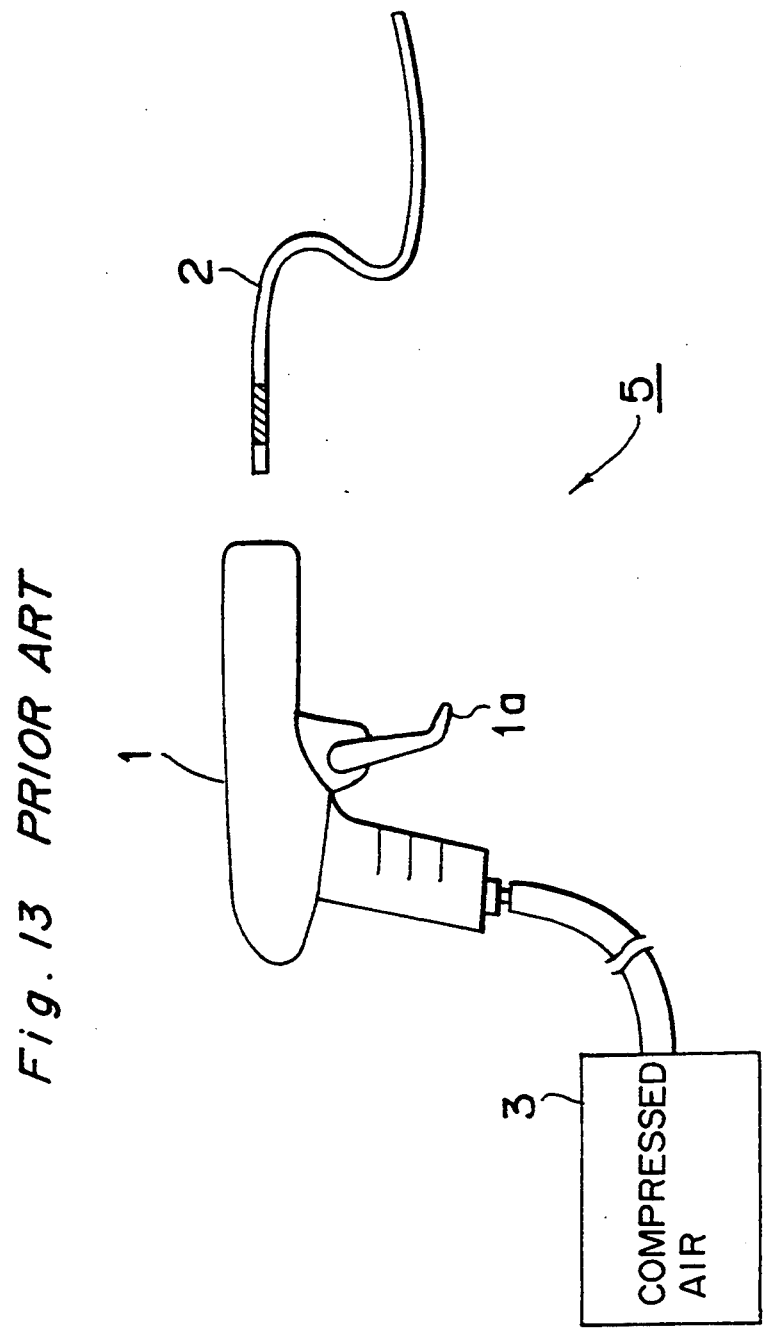

The powder-feeding apparatus is described with reference to FIG. 13. As shown in FIG. 13, this powder-feeding apparatus 5 is formed into a pistol shape provided with a compressed air supply source 3 and a lever 1a. The powder-feeding apparatus 5 comprises a regulator 1 which is connected to the compressed air supply source 3, for example, via a rubber tube and which regulates the transmission of compressed air fed from the compressed air supply source 3 by the way how to pull the lever 1a, and a medicament feed tube 2 which is connected to the regulator 1 and which serves to feed medicament to an affected part in the body. In such a powder-feeding apparatus, powdered medicament or the like is first charged within the medicament feed tube 2. Then the medicament feed tube 2 is connected to the regulator 1. By operating the lever 1a to transmit the compressed air from the regulator 1, the powdered medicament or the like within the chemicals feed tube 2 is injected to the affected part together with the compressed air.

There are also available such types of apparatus that a small-size gas cylinder is used as the compressed air supply source so that the overall size of the apparatus is reduced smaller than the above powder-feeding apparatus 5.

Some of the above-described conventional powder-feeding apparatus are simply designed to push out medicament contained in the tube with air fed to the tube, while others have the structure, formation, and operation similar to those of, for example, painting-use sprayers to be used for applying paints. Accordingly, in a powder-feeding apparatus of such a type that the medicament within the tube are pushed out with air, too small amount of medicament charged in the tube would make it less expected for patients to have effective medical treatment, while too large amounts of medicament would cause the tube to be clogged with the medicament so that the medicament will not be pushed out of the tube. As a result, the conventional powder-feeding apparatuses have been required to regulate the amount of medicament to be discharged in the tube, as a problem. Besides, in so-called painting-use powder-feeding apparatuses of the sprayer type, medicament is sucked out by the flow of compressed air fed and transmitted together with the compressed air, in which case the compressed air is required to have a higher than specified flow velocity to suck out the medicament. As a result, the flow rate of the compressed air is increased so that disadvantages may arise in powder-feeding to affected parts in the body, as a problem. Moreover, powder feed would be impossible when the medicament have been solidified, as another problem.

As described above, the conventional powder-feeding apparatuses have poor operability for use in actual medical treatment, and are in some cases improper as a curing apparatus.

SUMMARY OF THE INVENTION

The present invention has been achieved with a view to solving these and other problems. An object of the present invention is therefore to provide a powdered medicament-mixed gas injecting apparatus which has good operability and which is proper as a curing apparatus, and also to provide a powdered medicament-mixed gas injecting nozzle to be used in the powdered medicament-mixed gas injecting apparatus.

To accomplish the above object, according to one aspect of the present invention, there is provided a powdered medicament-mixed gas injecting apparatus comprising: a first passage having at one end thereof a gas supply opening for supplying gas; a second passage having at one end thereof a container-fitting end portion for fitting thereto a container opening of a powdered medicament container in which powdered medicament is accommodated and which has one end closed and the other end provided with the container opening, the other end of the second passage being coupled with the other end of the first passage, the second passage serving for introducing supply gas fed from the gas supply opening of the first passage to the powdered medicament container and besides for introducing powdered medicament-mixed gas which has been formed by mixing the supply gas with the powdered medicament, in a direction opposite to a direction in which the supply gas is fed, and the second passage allowing gas to pass bidirectionally therethrough; and a third passage having one end thereof coupled with a coupling portion at which the respective other ends of the first and second passages are coupled with each other, where the third passage is branched from the coupling portion, the third passage having at the other end thereof a third passage opening for jetting out the powdered medicament-mixed gas for introducing the powdered medicament-mixed gas.

According to another aspect of the present invention, there is provided a cylindrical powdered medicament-mixed gas injecting nozzle used to the powdered medicament-mixed gas injecting apparatus according to this invention, one end of the nozzle is connected to the apparatus, and the nozzle comprises at the other end thereof a flat plate extending in a direction crossing a direction in which the cylindrical powdered medicament-mixed gas injecting nozzle extends, wherein one end of a passage extending in the cylindrical powdered medicament-mixed gas injecting nozzle is connected to the third passage opening and the other end thereof is opened at the flat plate in order to inject the powdered medicament-mixed gas.

Gas fed via the first passage is introduced through the second passage to the powdered medicament container fitted at the container-fitting end portion located at one end of the second passage. The gas introduced to the powdered medicament container stirs the powdered medicament accommodated in the powdered medicament container, and is transmitted from the powdered medicament container as powdered medicament-mixed gas, passing through the second passage. Thus, the second passage acts in such a way that supply gas supplied through the first passage and powdered medicament-mixed gas whose feed direction is reverse to that of the supply gas are allowed to pass therethrough in bidirectional, i.e., two-way fashion. The third passage acts to lead the powdered medicament-mixed gas to outside of the powdered medicament-mixed gas injecting apparatus.

In this way, the first to third passages act to aggressively stir the powdered medicament accommodated in the powdered medicament container and thereafter send the powdered medicament to the affected part.

BRIEF DESCRIPTION OF THE DRAWINGS

These and other objects and features of the present invention will become clear from the following description taken in conjunction with the preferred embodiments thereof with reference to the accompanying drawings, in which:

FIG. 1 is a perspective view showing an embodiment of the powdered medicament-mixed gas injecting apparatus according to the present invention and an embodiment of the powdered medicament-mixed gas injecting nozzle to be used in the powdered medicament-mixed gas injecting apparatus;

FIG. 2 is a plan view of the powdered medicament-mixed gas injecting apparatus shown in FIG. 1;

FIG. 3 is a front view of the powdered medicament-mixed gas injecting apparatus shown in FIG. 1;

FIG. 4 is a side view of the powdered medicament-mixed gas injecting apparatus shown in FIG. 1;

FIG. 5 is a view showing the internal structure of the powdered medicament-mixed gas injecting apparatus shown in FIG. 1 and further showing how the passage unit, the powdered medicament container, and the nozzle are fitted to the powdered medicament-mixed gas injecting apparatus;

FIG. 6 is a plan view of the passage unit fitted to the powdered medicament-mixed gas injecting apparatus shown in FIG. 1;

FIG. 7 is a left side view having a partial cross section of the passage unit shown in FIG. 6;

FIG. 8 is a sectional view taken along the line VIII—VIII of the passage unit shown in FIG. 6;

FIG. 9 is a block diagram showing the arrangement of the powdered medicament-mixed gas injecting apparatus shown in FIG. 1;

FIG. 10 is a view for explaining the flow of air in the passage unit, the powdered medicament container, and the nozzle as shown in FIG. 6;

FIG. 11 is a sectional view of the passage unit showing another example of a passage arrangement in the passage unit shown in FIG. 6;

FIG. 12 is a sectional view of the passage unit showing still another example of passage arrangement in the passage unit shown in FIG. 6; and FIG. 13 is a view showing the arrangement of the conventional powder-feeding apparatus.

DETAILED DESCRIPTION OF THE PREFERRED EMBODIMENTS

Before the description of the present invention proceeds, it is to be noted that like parts are designated by like reference numerals throughout the accompanying drawings.

An embodiment of the powdered medicament-mixed gas injecting apparatus of the present invention is described below with reference to the accompanying drawings.

FIG. 1 shows an overall view of a powdered medicament-mixed gas injecting apparatus 100 of the present embodiment. The powdered medicament-mixed gas injecting apparatus 100, as illustrated in FIGS. 2 through 4, has a length L of 90 mm, a width W of 48 mm, and a height H of 157 mm and has a grip 10 formed at a lower portion of the powdered medicament-mixed gas injecting apparatus 100 so that the operator such as a doctor can grip the powdered medicament-mixed gas injecting apparatus 100. As shown in FIG. 5, the powdered medicament-mixed gas injecting apparatus 100 comprises: an air pump 20 for sucking air from within the powdered medicament-mixed gas injecting apparatus 100 by fluctuating a diaphragm and transmitting the air as air required for injecting the powdered medicament; an operation switch 25 for the air pump 20, which switch is turned ON only while being depressed, and is automatically returned to an OFF condition when the switch is not depressed; an illumination lamp 30 which is an electric lamp, LED (Light-Emitting Diode), or the like for illuminating the affected part to be injected with powdered medicament; an illumination switch 35 for the illumination lamp 30, which switch is fixed ON or OFF; and a battery 40 which is the power supply for supplying the air pump 20 and the illumination lamp 30 with electric power.

In view of operability and the like, the operation switch 25 for the air pump 20 and the illumination switch 35 for the illumination lamp 30 are located on a front face 11*a* in a center portion 11 of the powdered medicament-mixed gas injecting apparatus 100 in proximity to the grip 10 of the powdered medicament-mixed gas injecting apparatus 100. The illumination lamp 30 is located on a front face 12*a* in an upper portion 12 of the powdered medicament-mixed gas injecting apparatus 100.

The air pump 20 is disposed in a rear portion 13 of the powdered medicament-mixed gas injecting apparatus 100 internally of the powdered medicament-mixed gas injecting apparatus 100 over a range from the upper portion 12 to the center portion 11. The battery 40 is disposed internally of the grip 10 of the powdered medicament-mixed gas injecting apparatus 100. The battery 40 is loaded to the interior of the powdered medicament-mixed gas injecting apparatus 100 by opening a battery-exchange use cover 15 which is provided in a rear face 14 of the powdered medicament-mixed gas injecting apparatus 100. As shown in FIG. 9, the output side of the battery 40 is connected to the air pump 20 via the operation switch 25 and, moreover, connected to the illumination lamp 30 via the illumination switch 35. It is noted that electrical wiring disposed between the air pump 20, the operation switch 25 for the air pump, the illumination lamp 30, the illumination switch 35, and the battery 40 is omitted in illustration in FIG. 5.

The rate of air feed of the air pump 20 is about 45 ml/sec, which corresponds to one several tenths of that of the above-described conventional powder-feeding apparatus.

As shown in FIGS. 2 through 5, on a top surface 12*b* of the powdered medicament-mixed gas injecting apparatus 100 there is formed a recess 16 to which a passage unit 50 will be fitted removably. On a bottom surface 16a of the recess 16, an insertion hole 17 of an about 5 mm inner diameter is formed vertically, to which an insertion-use protrusion 51 provided to the passage unit 50, which will be detailed later, will be removably fitted. An air inlet hole 17a having an inner diameter of approximately 1.5 mm is formed in the bottom surface of the insertion hole 17. Air transmitted from the air pump 20 via a tube 21 which is connected to a discharge outlet of the air pump 20 is supplied to the air inlet hole 17a. Further, in order that the airtightness between the inner circumferential surface of the insertion hole 17 and the outer circumferential surface of the insertion-use protrusion 51 is maintained when the insertion-use protrusion 51 is inserted into the insertion hole 17, an O-ring 18 is provided on the inner circumferential surface of the insertion hole 17 circumferentially of the inner circumferential surface.

Figure 6:
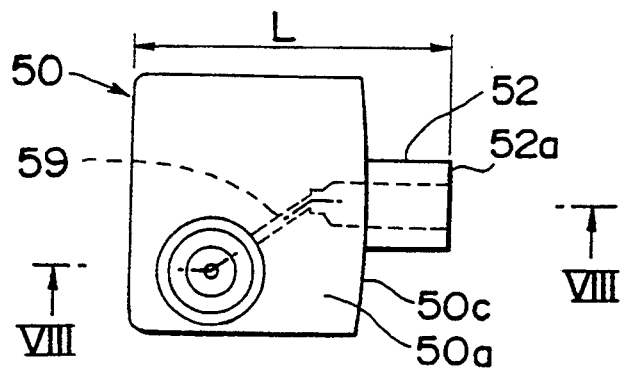
Figure 7:
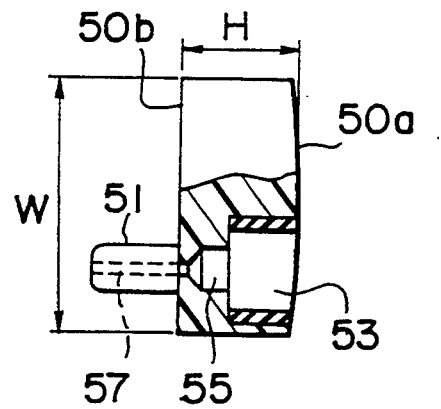

As shown in FIGS. 6 and 7, the passage unit 50 has a length L of 39 mm, a height H of 14 mm, and a width W of 31 mm. The aforementioned insertion-use protrusion 51 having a diameter of approximately 5 mm is protrudingly provided on a lower surface 50b of the passage unit 50. A nozzle fitting portion 52 having a diameter of approximately 10 mm is protrudingly provided on a front face 50c of the passage unit 50 which will be located on the front face 12a side of the powdered medicament-mixed gas injecting apparatus 100 when the passage unit 50 is fitted to the recess 16. In the passage unit 50 of such an arrangement, a powdered medicament container 70, in which powdered medicament such as hemostatics is accommodated, will be fitted into a container-fitting hole 53, which will be described later, and a nozzle for introducing powdered medicament-mixed air to an affected part will be inserted into the nozzle fitting portion 52.

On an upper surface 50a of the passage unit 50 and in a position decentered from the center line passing the midpoint of the width W and extending in the lengthwise direction, the container-fitting hole 53 which is a circular hole for inserting the opening of the powdered medicament container 70 and which forms an end of a later-described second passage is formed vertically. The container-fitting hole 53 has a depth corresponding to approximately a half of the aforementioned height H. A packing 54 which is made of silicone rubber is attached to the entire inner circumferential surface of the container-fitting hole 53 so that the opening of the powdered medicament container 70 can be fitted to the container-fitting hole 53 in an airtight manner.

The reason why the container-fitting hole 53 is provided in a position decentered from the center line is as follows. When the passage unit 50 is fitted to the recess 16 of the powdered medicament-mixed gas injecting apparatus 100, the center line of the passage unit 50 coincides with the center line of the powdered medicament-mixed gas injecting apparatus 100. In the case where a doctor uses the powdered medicament-mixed gas injecting apparatus 100, his eye is positioned in the direction of arrow B as shown in FIG. 1. So, if the container-fitting hole 53 was provided on the center line, the visual field of the doctor might be interrupted by the powdered medicament container 70 fitted to the container-fitting hole 53. To avoid this alignment situation, the container-fitting hole 53 is positioned to the decentered from the center line.

Figure 8:
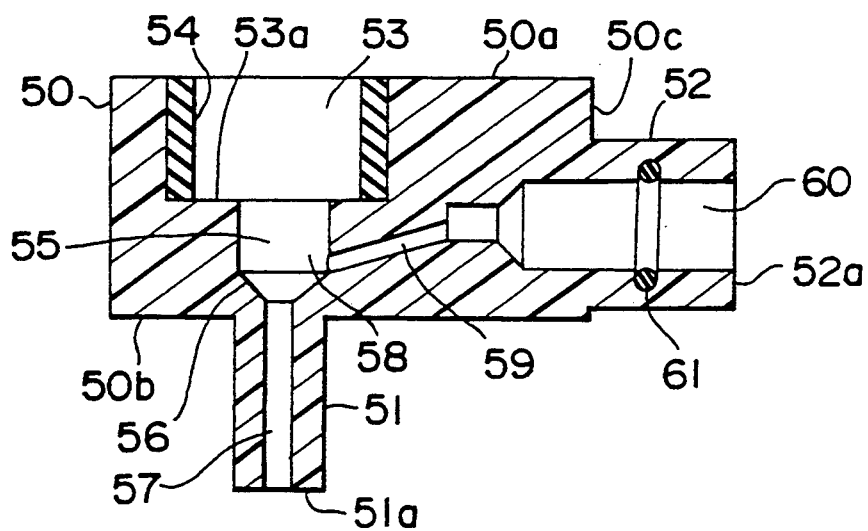
Figure 9:
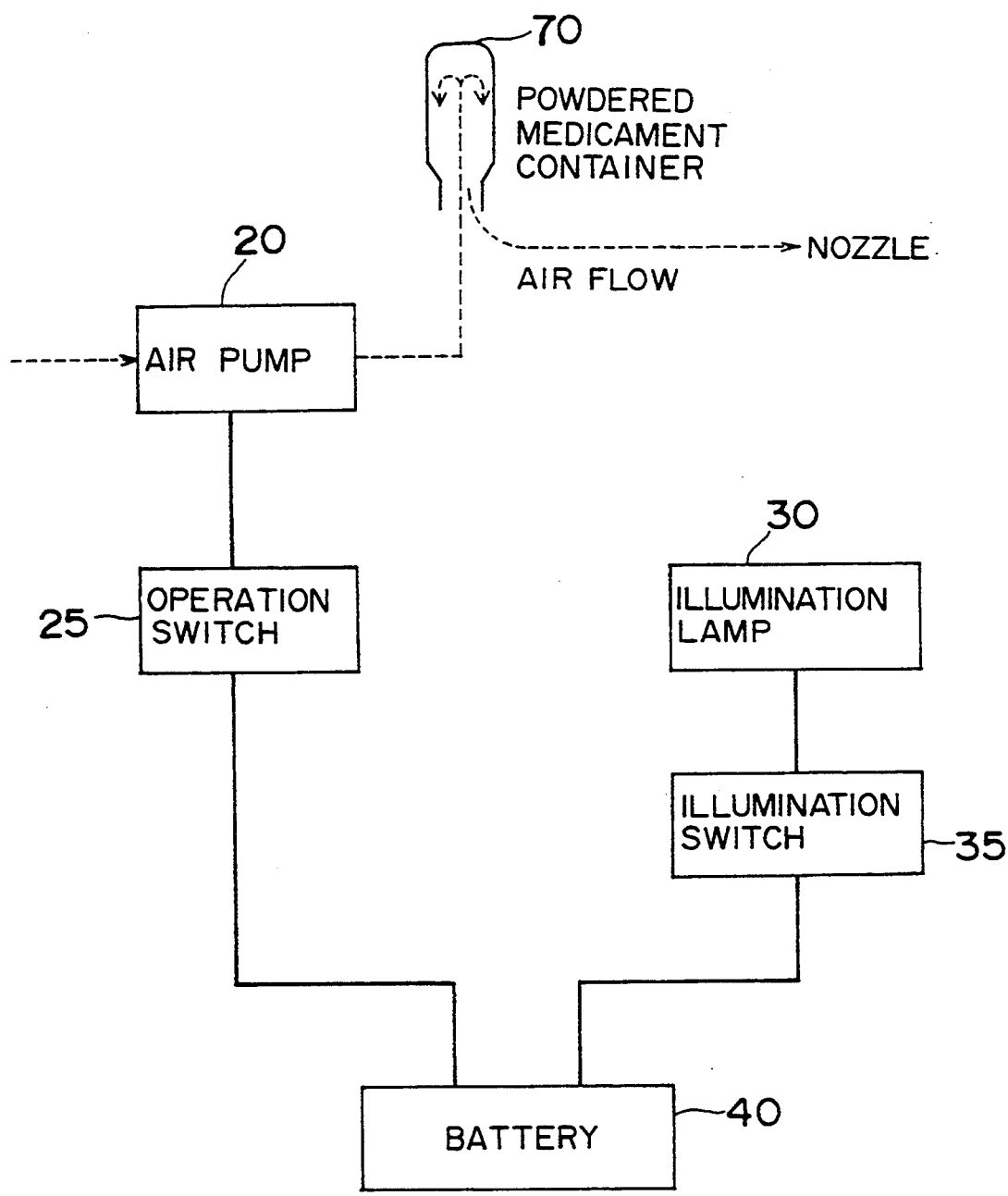
Figure 11:
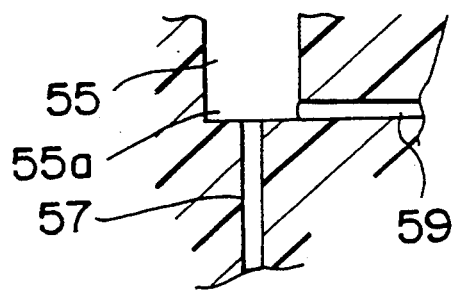

As shown in FIG. 8, in a center portion of a bottom surface 53a of the container-fitting hole 53, a passage 55 having an inner diameter of approximately 5.5 mm is formed vertically from the center portion of the bottom surface up to a depth approximately intermediate between the bottom surface 53a and the lower surface 50b of the passage unit 50. Further, at the other end of the passage 55, a first passage 57 having an inner diameter of approximately 1.5 mm is formed vertically via a conical portion 56. The conical portion 56 is provided in terms of machining work, and the other end 55a of the passage 55 may be flat as shown in FIG. 11. Also, the first passage 57 is so formed to extend along the axial center portion of the insertion-use protrusion 51 in the axial direction, one end of the first passage 57 is opened to an end face 51a of the insertion-use protrusion 51.

It is noted that a second passage is defined by the container-fitting hole 53 and the passage 55 in the present embodiment.

Also in the present embodiment, the container-fitting hole 53 and the passage 55 are connected directly to each other without any intervening means. However, the container-fitting hole 53 of a tube or the like and the passage 55 may also be connected to each other with a tube, other passage, or the like.

Further, a third passage comprising a passage 59 and a third passage opening 60 are formed in the interior of the passage unit 50.

Figure 10:
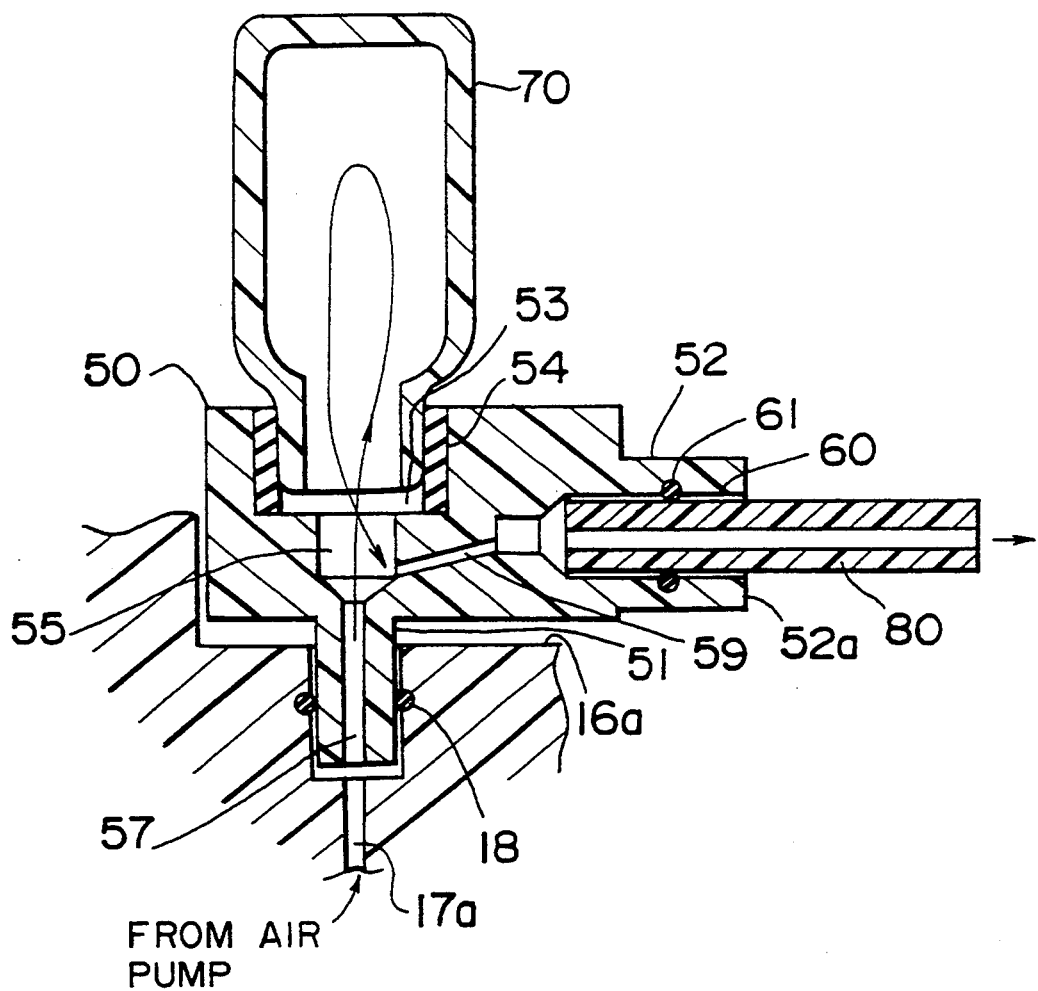

The third passage opening 60 is a hole having a diameter of approximately 5.5 mm bored in a center portion of the nozzle fitting portion 52 along the center line extending axially of the nozzle fitting portion 52 from a front face 52a of the nozzle fitting portion 52. Into the third passage opening 60 of such arrangement, an end of a cylindrical nozzle 80, for example as shown in FIG. 10, is inserted removably. Also, in order to maintain the airtightness between the outer circumferential surface of the nozzle 80 and the inner circumferential surface of the third passage opening 60 when the nozzle 80 is inserted into the third passage opening 60, an O-ring 61 extending circumferentially of the third passage opening 60 is provided at a generally center point of the third passage opening 60 in its extending direction.

The passage 59 has an inner diameter of 1 mm. Its one end is opened to a coupling portion 58 contacting the first passage 57 and the passage 55, while the other end is opened to the third passage opening 60. The passage 59 couples the coupling portion 58, which is positioned away from the center line of the passage unit 50, and the third passage opening 60, which extends along the center line of the passage unit 50, with each other. In the present embodiment, as shown in FIG. 8, the passage 59 is given such a slight upward slant that the other end of the passage 59 at which the passage 59 is connected to the third passage opening 60 is positioned closer to the upper surface 50a of the passage unit 50, than the one end of the passage 59 at which the passage 59 is connected to the coupling portion 58. In addition, as shown in FIG. 11, the passage 59 may be without such an upward slant. Further, the inner diameter of the passage 59 is required only such that the inner diameter of the opening of the passage 59 at the coupling portion 58 is 1 mm and the rest of the inner diameter gradually increases along the extending direction of the passage 59.

In the above-described passage unit 50, the first passage 57 leads air transmitted from the air pump 20 to the second passage. The second passage leads the supply air from the first passage 57 toward the powdered medicament container 70 and besides leads powdered medicament-mixed air transmitted from the powdered medicament container 70 to the third passage. The third passage acts to lead the powdered medicament-mixed air to the nozzle 80.

It is noted that the second passage refers to a passage through which bidirectional air flow is allowed including one flow of supply air in a direction from the first passage 57 toward the powdered medicament container 70 and the other flow of powdered medicament-mixed air in a direction from the powdered medicament container 70 toward the third passage.

In the present embodiment, the third passage opening 60, which forms the third passage, serves also as a fitting portion for the nozzle 80. However, the nozzle may alternatively be connected to the third passage opening 60 in another embodiment.

Also, in the present embodiment, the flow velocity of air that passes through the first passage 57 can be increased by reducing the inner diameter of the first passage 57. Besides, the air jetted out from the first passage 57 can be made to flow toward the passage 55 by so arranging that the passage 55 and the first passage 57 are extended vertically while the passage 59 is extended generally horizontally.

Also, the inner diameters of the passage 55, the first passage 57, and the passage 59 are not limited to those described above. However, it is preferable that the inner diameter of the passage 55 is the largest of them so that the air that has passed through the first passage 57 is securely led toward the powdered medicament container 70.

Further, the flow-path cross sections of the passage 55, the first passage 57, and the passage 59 are not limited to circular-shaped ones.

Figure 12:
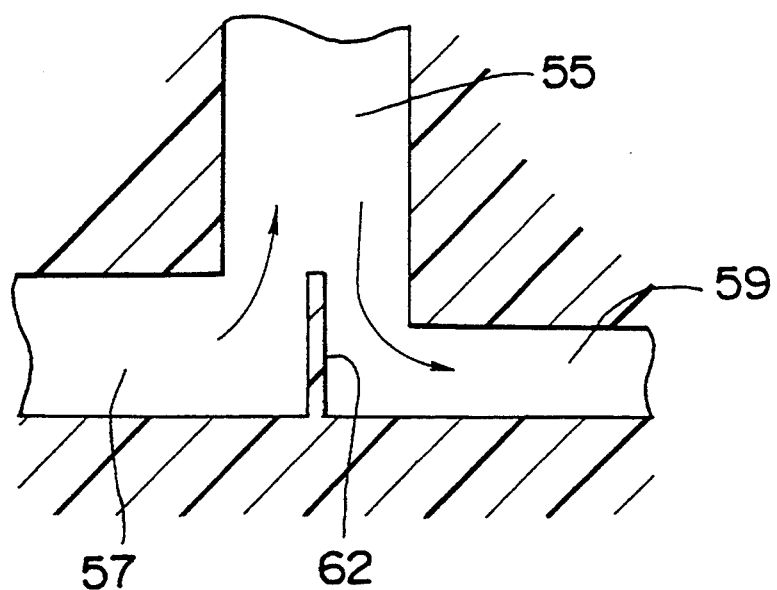

Further, in the passage unit 50, the container-fitting hole 53 is preferably extended vertically, while the passage 55 and the first passage 57 may also be extended horizontally. Besides, when the first passage 57 and the passage 59 are extended horizontally and the passage 55 is extended in a direction opposite to the direction of gravity with respect to the first passage 57 and the passage 59 as shown in FIG. 12, it is also possible to provide a partition plate 62.between the first passage 57 and the passage 59 so that the supply air led by the first passage 57 will flow to the passage 55.

It is noted that, instead of the nozzle 80, a medical-use beak tube, which is connected to an endoscope, may also be connected to the third passage opening 60.

With the use of the passage unit 50 and the air pump 20 according to the present embodiment, 500 mg of powdered medicament, such as for hemostatic use, accommodated in the powdered medicament container 70 will be injected out in around 4 seconds.

Next described is an embodiment of the nozzle to be inserted into the third passage opening 60.

A nozzle 85 as shown in FIG. 1, primarily for use in obstetrics and gynecology, comprises a cylindrical portion 85a of a cylindrical shape and a flat plate 85b of a circular shape provided at an end of the cylindrical portion 85a, which are made of, for example, polyethylene. Also, a through hole extending along a central interior of the cylindrical portion 85a axially of the cylindrical portion 85a and serving for leading the powdered medicament-mixed air to the affected part is opened in a front face 85c of the flat plate 85b in a position decentered from the flat plate 85b. The reason why the through hole has been decentered from the flat plate 85b is to prevent the possibility that the flat plate 85b may in some cases interrupt the visual field of the doctor during medical treatment. Further, the flat plate 85b is to keep the powdered medicament, which has been injected and scattered to the affected part, pressed onto the affected part.

The powdered medicament-mixed gas injecting apparatus 100 as described above is now described with regard to its operation. It is noted that the powdered medicament-mixed gas injecting apparatus 100 has previously been loaded with a specified battery.

Figure 5:
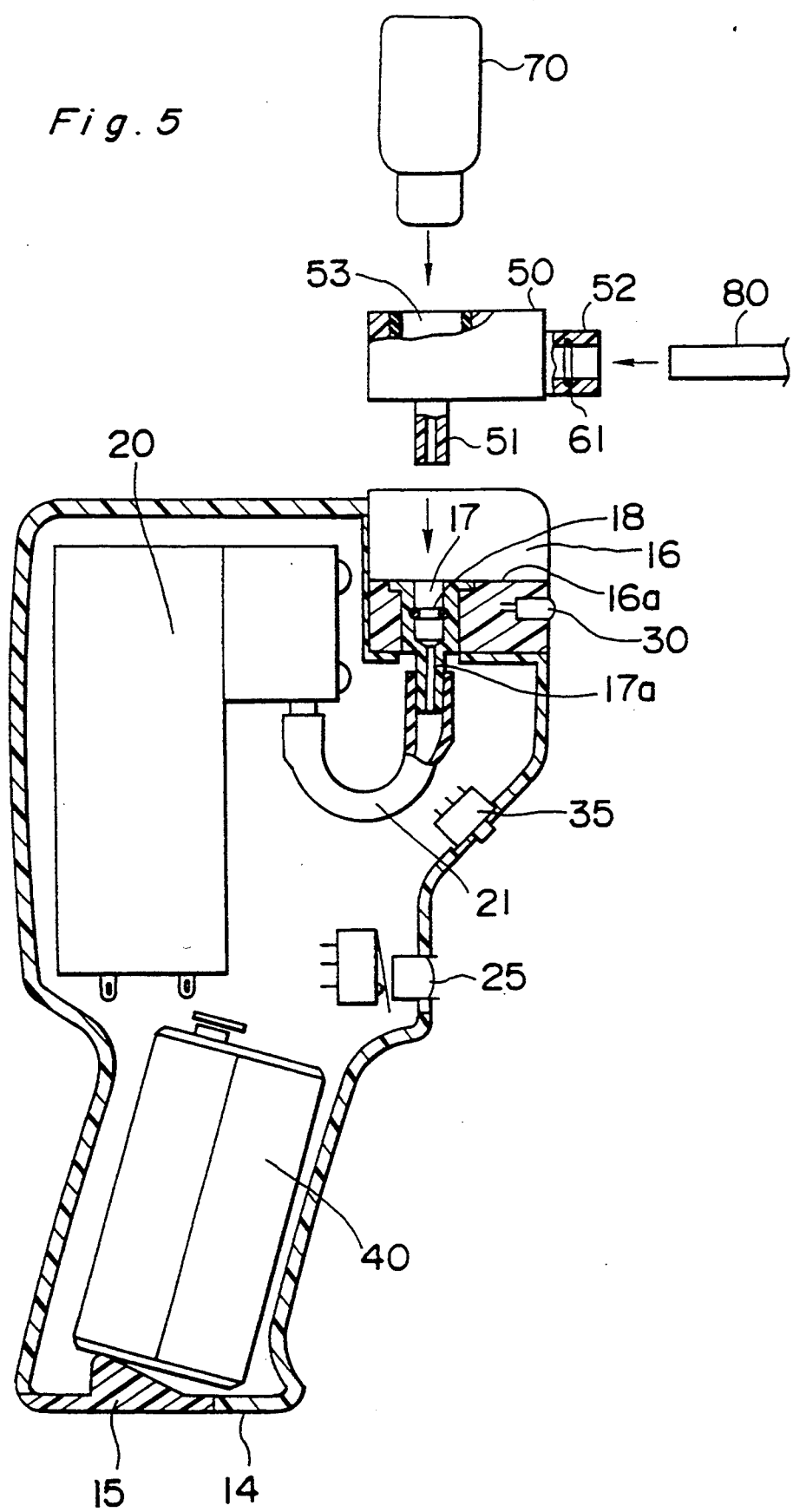

As shown in FIG. 5, the operator fits a new passage unit 50 to the recess 16 of the powdered medicament-mixed gas injecting apparatus 100 in such a way that the insertion-use protrusion 51 of the passage unit 50 is inserted into the insertion hole 17 of the recess 16 of the powdered medicament-mixed gas injecting apparatus 100. Over this operation, the insertion hole 17 and the insertion-use protrusion 51 are maintained airtight by the O-ring 18, while the insertion-use protrusion 51 is securely fixed into the insertion hole 17.

Further, the operator inserts the opening of the powdered medicament container 70, in which powdered medicament is accommodated, into the container-fitting hole 53 of the passage unit 50. Over this operation, the opening of the powdered medicament container 70 and the container-fitting hole 53 are maintained airtight by the packing 54, while the powdered medicament container 70 is securely fixed into the container-fitting hole 53.

Further, the operator inserts an end portion of the aforementioned nozzle 85 into the third passage opening 60 of the nozzle fitting portion 52 of the passage unit 50. Over this operation, the nozzle 85 and the third passage opening 60 are maintained airtight by the O-ring 61, while the nozzle 85 is securely fixed into the third passage opening 60.

It is noted that with the powdered medicament container 70 fitted into the container-fitting hole 53, the powdered medicament accommodated in the powdered medicament container 70 has dropped by gravity down to the conical portion 56 level as shown in FIG. 8.

In such a state, the doctor inserts the nozzle 85 into the body so that the end portion of the nozzle 85 is opposed to the affected part. Also, if necessary, the doctor operates the illumination switch 35 to turn on the illumination lamp 30. After such operation, the doctor depresses the operation switch 25 to actuate the air pump 20 of the powdered medicament-mixed gas injecting apparatus 100.

With the air pump 20 commencing operation, the air pump 20 transmits air, which the air pump 20 has sucked in while sucking the air within the powdered medicament-mixed gas injecting apparatus 100, through the discharge outlet of the air pump 20. The air transmitted from the air pump 20 is introduced to the air inlet hole 17a via the tube 21 and then supplied to the first passage 57 of the passage unit 50 through the air inlet hole 17a.

By the arrangement that the inner diameter of the passage 55 is much larger than that of the passage 59 that leads to the third passage opening 60, and that the inner diameter of the first passage 57 is reduced so that the flow velocity of the air passing through the first passage 57 is increased, most of the supply air fed to the first passage 57 is supplied to the passage 55, flowing through the passage 55 toward the powdered medicament container 70. In this process, the supply air goes forward while stirring the powdered medicament that has dropped to the passage 55. The supply air further stirs the powdered medicament supplied into the powdered medicament container 70 and accommodated in the powdered medicament container 70. By the supply air being injected into the powdered medicament container 70 in this way, the pressure within the powdered medicament container 70 is increased. As a result, the air within the powdered medicament container 70 is directed as a powdered medicament-mixed air in which the powdered medicament have been mixed, toward the passage 59 which is the only passage that leads to low-pressure outside of the powdered medicament-mixed gas injecting apparatus 100, and flows through the passage 55 in a direction opposite to the direction in which the supply air flows, while stirring the powdered medicament which has dropped to the passage 55. Then, the powdered medicament-mixed air led to the passage 59 is fed to the third passage opening 60, and injected and scattered to the affected part in the body via the through hole of the nozzle 85 that has been inserted into the third passage opening 60.

The doctor, after injecting a necessary amount of powder medicament, stops the operation switch 25 from being depressed, thus stopping the air pump 20. In this process, such an operation may also be performed, if necessary, that the injected powdered medicament is pressed against the affected part by the flat plate **85*b* at the end of the nozzle 85. At a point in time when the above-described specified procedure is completed, the doctor withdraws the nozzle 85** from within the body, ending the medical treatment.

After the medical treatment has been completed, the passage unit 50 is withdrawn from the recess 16 of the powdered medicament-mixed gas injecting apparatus 100 and discarded.

As described above, according to the powdered medicament-mixed gas injecting apparatus 100 of the present embodiment, the powdered medicament-mixed gas injecting apparatus 100 comprises the air pump 20, the passage unit 50, and the like, so that powdered medicament can be injected to the affected part with good operability.

Also, according to the powdered medicament-mixed gas injecting apparatus 100 of the present embodiment, the powdered medicament to be injected can be injected and scattered to the affected part via a nozzle after being stirred mainly within the powdered medicament container 70.

Further, in the powdered medicament-mixed gas injecting apparatus 100 of the present embodiment, the flow rate of air per unit time of the air pump 20 is much less than that of the conventional powder-feeding apparatus as described above. Accordingly, when powdered medicament is injected and scattered to affected parts, such as the stomach and the colon, a less amount of air is supplied to within the body so that bad effects on these organs can be suppressed to a minimum.

Also, according to the powdered medicament-mixed gas injecting apparatus 100 of the present embodiment, the passage unit 50 is freely exchangeable against the powdered medicament-mixed gas injecting apparatus 100, thus free from troubles in terms of sanitation.

Also, in the present embodiment, supply air and powdered medicament-mixed air have been so arranged to flow bidirectionally through one passage 55. Instead, there may be provided two passages, one passage for supply air and the other passage for powdered medicament-mixed air.

Also, the powdered medicament-mixed gas injecting apparatus may be so arranged that a gas supply source provided externally of the powdered medicament-mixed gas injecting apparatus 100 instead of the air pump 20 and the insertion-use protrusion 51 of the passage unit 50 are connected to each other so that gas can be supplied to the first passage 57. In such an arrangement, not only air but special gases as well may be supplied to the passage unit 50.

Also, according to the nozzle 85 of the present embodiment, the flat plate **85*b* at the end of the nozzle 85 is provided so as to be decentered with respect to the cylindrical portion 85*a*. Accordingly, the visual field of the doctor will not be interrupted by the flat plate 85*b*** during medical treatment, so that the powdered medicament-mixed gas injecting process can be carried out with good operability.

As described in detail above, according to the present invention, gas supplied via the first passage is led via the second passage to the powdered medicament container fitted to the container-fitting end portion provided at an end of the second passage. Then the gas, stirring the powdered medicament accommodated in the powdered medicament container, is transmitted as a powdered medicament-mixed gas from the powdered medicament container, and is sent out of the powdered medicament-mixed gas injecting apparatus through the third passage. Accordingly, the powdered medicament-mixed gas injecting apparatus of the present invention can aggressively stir the powdered medicament accommodated in the powdered medicament container and thereafter supply powdered medicament to the affected part. Thus, the powdered medicament-mixed gas injecting apparatus of the present invention is free from the possibility that the powdered medicament is solidified and, as a result, will no longer be fed. Further, the powdered medicament-mixed gas injecting apparatus only requires less a small amount of gas used by virtue of its arrangement wherein powdered medicament is fed and is not sucked out. Furthermore, the apparatus can feed a necessary amount of powdered medicament without the need of controlling the amount of powdered medicament.

Although the present invention has been fully described in connection with the preferred embodiments thereof with reference to the accompanying drawings, it is to be noted that various changes and modifications are apparent to those skilled in the art. Such changes and modifications are to be understood as included within the scope of the present invention as defined by the appended claims unless they depart therefrom.

What is claimed is:

1. A powdered medicament-mixed gas injecting apparatus comprising:

- a first passage having at one end thereof a gas supply opening for supplying gas;
- a second passage having at one end thereof a container-fitting end portion for fitting thereto a container opening of a powdered medicament container in which powdered medicament is accommodated and which has one end closed and the other end provided with the container opening, the other end of the second passage being coupled with the other end of the first passage, the second passage serving for introducing supply gas fed from the gas supply opening of the first passage to the powdered medicament container and for introducing powdered medicament-mixed gas which has been formed by mixing the supply gas with the powdered medicament, in a direction opposite to a direction in which the supply gas is fed, and the second passage allowing gas to pass bidirectionally therethrough; and a third passage having one end thereof coupled with a coupling portion at which the respective other ends of the first and second passages are coupled with each other, where the third passage is branched from the coupling portion, the third passage having at the other end thereof a third passage opening for jetting out the powdered medicament-mixed gas to introducing the powdered medicament-mixed gas.

2. The powdered medicament-mixed gas injecting apparatus according to claim 1, wherein among a first passage sectional area, which is a sectional area of a cross section of the first passage, a second passage sectional area, which is a sectional area of a cross section of the second passage, and a third passage inlet sectional area, which is a sectional area of a cross section of the coupling portion of the third passage, the third passage inlet sectional area is the smallest.

3. The powdered medicament-mixed gas injecting apparatus according to claim 2, wherein among the first passage sectional area, the second passage sectional area, and the third passage inlet sectional area, the second passage sectional area is the largest.

4. The powdered medicament-mixed gas injecting apparatus according to claim 1, further comprising a gas feed pump connected to the gas supply opening of the first passage and serving for supplying gas.

5. The powdered medicament-mixed gas injecting apparatus according to claim 2, further comprising a gas feed pump connected to the gas supply opening of the first passage and serving for supplying gas.

6. The powdered medicament-mixed gas injecting apparatus according to claim 4, further comprising:
power supply for supplying electric power to the gas feed pump; and
an illumination unit for illuminating an affected part to which the powdered medicament-mixed air fed from the third passage opening is to be injected, wherein the illumination unit will emit light with electric power supplied from the power supply.

7. The powdered medicament-mixed gas injecting apparatus according to claim 5, further comprising:
power supply for supplying electric power to the gas feed pump; and
an illumination unit for illuminating an affected part to which the powdered medicament-mixed air fed from the third passage opening is to be injected, wherein the illumination unit will emit light with electric power supplied from the power supply.

8. The powdered medicament-mixed gas injecting apparatus according to claim 6, wherein the first through third passages are formed in a passage unit and the passage unit is removable from a body of the powdered medicament-mixed gas injecting apparatus with which the gas feed pump, the power supply, and the illumination unit are provided.

9. The powdered medicament-mixed gas injecting apparatus according to claim 7, wherein the first through third passages are formed in a passage unit and the passage unit is removable from a body of the powdered medicament-mixed gas injecting apparatus with which the gas feed pump, the power supply, and the illumination unit are provided.

10. A cylindrical powdered medicament-mixed gas injecting nozzle used for a powdered medicament-mixed gas injecting apparatus comprising:

a first passage having at one end thereof a gas supply opening for supplying gas;

a second passage having at one end thereof a container-fitting end portion for fitting thereto a container opening of a powdered medicament container in which powdered medicament is accommodated and which has one end closed and the other end provided with the container opening, the other end of the second passage being coupled with the other end of the first passage, the second passage serving for introducing supply gas fed from the gas supply opening of the first passage to the powdered medicament container and for introducing powdered medicament-mixed gas which has been formed by mixing the supply gas with the powdered medicament, in a direction opposite to a direction in which the supply gas is fed, and the second passage allowing gas to pass bidirectionally therethrough; and a third passage having one end thereof coupled with a coupling portion at which the respective other ends of the first and second passages are coupled with each other, where the third passage is branched from the coupling portion, the third passage having at the other end thereof a third passage opening for jetting out the powdered medicament-mixed gas to introducing the powdered medicament-mixed gas, the cylindrical powdered medicament-mixed gas injecting nozzle being connected to the apparatus, and comprising at one end thereof a flat plate extending in a direction crossing a direction in which the cylindrical powdered medicament-mixed gas injecting nozzle extends, wherein one end of a passage extending in the cylindrical powdered medicament-mixed gas injecting nozzle is connected to the third passage opening and the other end thereof is opened at the flat plate in order to inject the powdered medicament-mixed gas.

11. The cylindrical powdered medicament-mixed gas injecting nozzle used to the powdered medicament-mixed gas injecting apparatus according to claim 10, wherein in the apparatus among a first passage sectional area, which is a sectional area of a cross section of the first passage, a second passage sectional area, which is a sectional area of a cross section of the second passage, and a third passage inlet sectional area, which is a sectional area of a cross section of the coupling portion of the third passage, the third passage inlet sectional area is the smallest, the cylindrical powdered medicament-mixed gas injecting nozzle being connected to the apparatus, and comprising at one end thereof a flat plate extending in a direction crossing a direction in which the cylindrical powdered medicament-mixed gas injecting nozzle extends, wherein one end of a passage extending in the cylindrical powdered medicament-mixed gas injecting nozzle is connected to the third passage opening and the other end thereof is opened at the flat plate in order to inject the powdered medicament-mixed gas.

12. The cylindrical powdered medicament-mixed gas injecting nozzle used for the powdered medicament-mixed gas injecting apparatus according to the claim 11, wherein in the apparatus further comprising a gas feed pump connected to the gas supply opening of the first passage and serving for supplying gas, the cylindrical powdered medicament-mixed gas injecting nozzle being connected to the apparatus, and comprising at one end thereof a flat plate extending in a direction crossing a direction in which the cylindrical powdered medicament-mixed gas injecting nozzle extends, wherein one end of a passage extending in the cylindrical powdered medicament-mixed gas injecting nozzle is connected to the third passage opening and the other end thereof is opened at the flat plate in order to inject the powdered medicament-mixed gas.

13. The cylindrical powdered medicament-mixed gas injecting nozzle used for the powdered medicament-mixed gas injecting apparatus according to claim 12, wherein in the apparatus further comprising power supply for supplying electric power to the gas feed pump; and an illumination unit for illuminating an affected part to which the powdered medicament-mixed air fed from the third passage opening is to be injected, wherein the illumination unit will emit light with electric power supplied from the power supply, the cylindrical powdered medicament-mixed gas injecting nozzle being connected to the apparatus, and comprising at one end thereof a flat plate extending in a direction crossing a direction in which the cylindrical powdered medicament-mixed gas injecting nozzle extends, wherein one end of a passage extending in the cylindrical powdered medicament-mixed gas injecting nozzle is connected to the third passage opening and the other end thereof is opened at the flat plate in order to inject the powdered medicament-mixed gas.

14. The cylindrical powdered medicament-mixed gas injecting nozzle used for the powdered medicament-mixed gas injecting apparatus according to claim 13, wherein the first through third passages being formed in a passage unit and the passage unit being removable from a body of the powdered medicament-mixed gas injecting apparatus with which the gas feed pump, the power supply, and the illumination unit are provide, the cylindrical powdered medicament-mixed gas injecting nozzle being connected to the apparatus, and comprising at one end thereof a flat plate extending in a direction crossing a direction in which the cylindrical powdered medicament-mixed gas injecting nozzle extends, wherein one end of a passage extending in the cylindrical powdered medicament-mixed gas injecting nozzle is connected to the third passage opening and the other end thereof is opened at the flat plate in order to inject the powdered medicament-mixed gas.

15. The cylindrical powdered medicament-mixed gas injecting nozzle according to claim 10, wherein the other end of the passage of the cylindrical powdered medicament-mixed gas injecting nozzle is opened at a portion away from a center portion of the flat plate.

16. The cylindrical powdered medicament-mixed gas injecting nozzle according to claim 11, wherein the other end of the passage of the cylindrical powdered medicament-mixed gas injecting nozzle is opened at a portion away from a center portion of the flat plate.

17. The cylindrical powdered medicament-mixed gas injecting nozzle according to claim 12, wherein the other end of the passage of the cylindrical powdered medicament-mixed gas injecting nozzle is opened at a portion away from a center portion of the flat plate.

18. The cylindrical powdered medicament-mixed gas injecting nozzle according to claim 13, wherein the other end of the passage of the cylindrical powdered medicament-mixed gas injecting nozzle is opened at a portion away from a center portion of the flat plate.

19. The cylindrical powdered medicament-mixed gas injecting nozzle according to claim 14, wherein the other end of the passage of the cylindrical powdered medicament-mixed gas injecting nozzle is opened at a portion away from a center portion of the flat plate.

* * * * *